(12) United States Patent
Lancaster et al.

(10) Patent No.: US 8,760,271 B2
(45) Date of Patent: Jun. 24, 2014

(54) METHODS AND SYSTEMS TO SUPPORT AUDITORY SIGNAL DETECTION

(75) Inventors: Jeff Lancaster, Plymouth, MN (US); Robert De Mers, Nowthen, MN (US)

(73) Assignee: Honeywell International Inc., Morristown, NJ (US)

( * ) Notice: Subject to any disclaimer, the term of this patent is extended or adjusted under 35 U.S.C. 154(b) by 309 days.

(21) Appl. No.: 13/293,838

(22) Filed: Nov. 10, 2011

(65) Prior Publication Data

US 2013/0120124 A1    May 16, 2013

(51) Int. Cl.
*G08B 3/00* (2006.01)

(52) U.S. Cl.
USPC .................. 340/384.1; 340/384.5; 381/57

(58) Field of Classification Search
USPC .......... 340/384.1, 384.5; 381/56, 57; 704/226, 704/235
See application file for complete search history.

(56) References Cited

U.S. PATENT DOCUMENTS

| | | | |
|---|---|---|---|
| 4,644,327 A | 2/1987 | Patterson | |
| 6,067,006 A * | 5/2000 | O'Brien | 340/384.1 |
| 6,259,792 B1 | 7/2001 | Lambrecht | |
| 6,360,187 B1 | 3/2002 | Hermann | |
| 7,268,671 B2 | 9/2007 | McDaniel et al. | |
| 7,346,172 B1 | 3/2008 | Begault | |
| 7,401,684 B2 | 7/2008 | Fujita | |
| 7,512,247 B1 * | 3/2009 | Odinak et al. | 381/312 |
| 7,933,420 B2 | 4/2011 | Copley et al. | |
| 2002/0097884 A1 | 7/2002 | Cairns | |
| 2007/0188308 A1 | 8/2007 | Lavoie | |
| 2007/0273556 A1 | 11/2007 | Gyde et al. | |
| 2008/0004872 A1 | 1/2008 | Nordholm et al. | |
| 2008/0240456 A1 | 10/2008 | Sakamoto et al. | |
| 2009/0189786 A1 | 7/2009 | Fabas et al. | |
| 2009/0274316 A1 | 11/2009 | Tran | |
| 2010/0146445 A1 * | 6/2010 | Kraut | 715/821 |
| 2010/0296668 A1 | 11/2010 | Lee et al. | |
| 2012/0281856 A1 * | 11/2012 | Georgiou et al. | 381/94.2 |

FOREIGN PATENT DOCUMENTS

GB    2084783 A    4/1982

OTHER PUBLICATIONS

EP Search Report, EP 12191511.0-1901 dated Jun. 3, 2013.
EP Office Action, EP 12 191 511.0 dated Mar. 22, 2013.

* cited by examiner

*Primary Examiner* — Brent Swarthout
(74) *Attorney, Agent, or Firm* — Ingrassia Fisher & Lorenz, P.C.

(57) ABSTRACT

Methods and apparatus are provided for producing an auditory alert that comprises sonic properties to an equipment operator wearing an auditory headset prior to the presentation of the auditory alert to the operator. The method comprises measuring an at-ear ambient noise spectrum, determining frequencies within the at-ear ambient noise spectrum that have relative minimum intensities and enhancing the magnitude of the determined relative minimum intensities. The method then generates the auditory alert incorporating the enhanced relative minimum intensities.

15 Claims, 3 Drawing Sheets

METHODS AND SYSTEMS TO SUPPORT AUDITORY SIGNAL DETECTION

TECHNICAL FIELD

The present invention generally relates to sound control within a confined space, and more particularly relates to methods and systems to enhance auditory detection of alerts by a wearer of a headset or in-ear device in the presence of ambient noise.

BACKGROUND

The ability of equipment operators to detect auditory alerts, such as cautions and warnings within a confined space while wearing headsets or other devices used for hearing protection and/or communication, can be compromised by inappropriate alert components coupled with the physical auditory damping characteristics of the device in the presence of ambient noise. Currently, the rudimentary solution is to set the amplifier gain of the alert to a very high level to overwhelm the ambient noise and penetrate the attenuation properties of a device. The result is an obnoxiously and unnecessarily loud alert signal, which can result in a "startle" response that may impact operational safety.

Accordingly, it is desirable to provide systems and methods to condition auditory alerts based on the spectral qualities and associated distribution of intensities of the ambient noise and the attenuation/amplification characteristics of an active noise reduction (ANR) or passive headset or other hearing protection device.

BRIEF SUMMARY

A method is provided for providing an auditory alert that comprises sonic properties to an equipment operator wearing a headset or other device that occludes the ear prior to the presentation of the auditory alert to the operator. The method comprises measuring an at-ear ambient noise spectrum, determining frequencies within the at-ear ambient noise spectrum that have relative minimum intensities, and enhancing the magnitude of the determined relative minimum intensities. The method then generates an auditory alert incorporating the enhanced relative minimum intensities.

A method is provided for producing an auditory alert that comprises sonic properties to an equipment operator wearing an auditory headset prior to the presentation of the auditory alert to the operator. The method comprises measuring an ambient noise spectrum in proximity to the equipment operator and outside an acoustic seal of the auditory headset, determining frequencies of an at-ear sound spectrum having relative minimum intensities from the ambient noise spectrum, and enhancing the magnitude of the determined relative minimum intensities of the at-ear sound spectrum. The method then generates the auditory alert including the enhanced relative minimum intensities.

A system is provided for producing an auditory alert comprising sonic properties to an equipment operator wearing an auditory headset prior to the presentation of the auditory alert to the operator. The system comprises a microphone and a computing device in operable communication with the microphone, wherein the computing device is configured to process sound data received from the microphone into an alert signal. The system further comprises a signal generator configured to create that alert signal and an alert annunciator configured to annunciate the signal.

Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The present invention will hereinafter be described in conjunction with the following drawing figures, wherein like numerals denote like elements.

DETAILED DESCRIPTION

Figure 1:
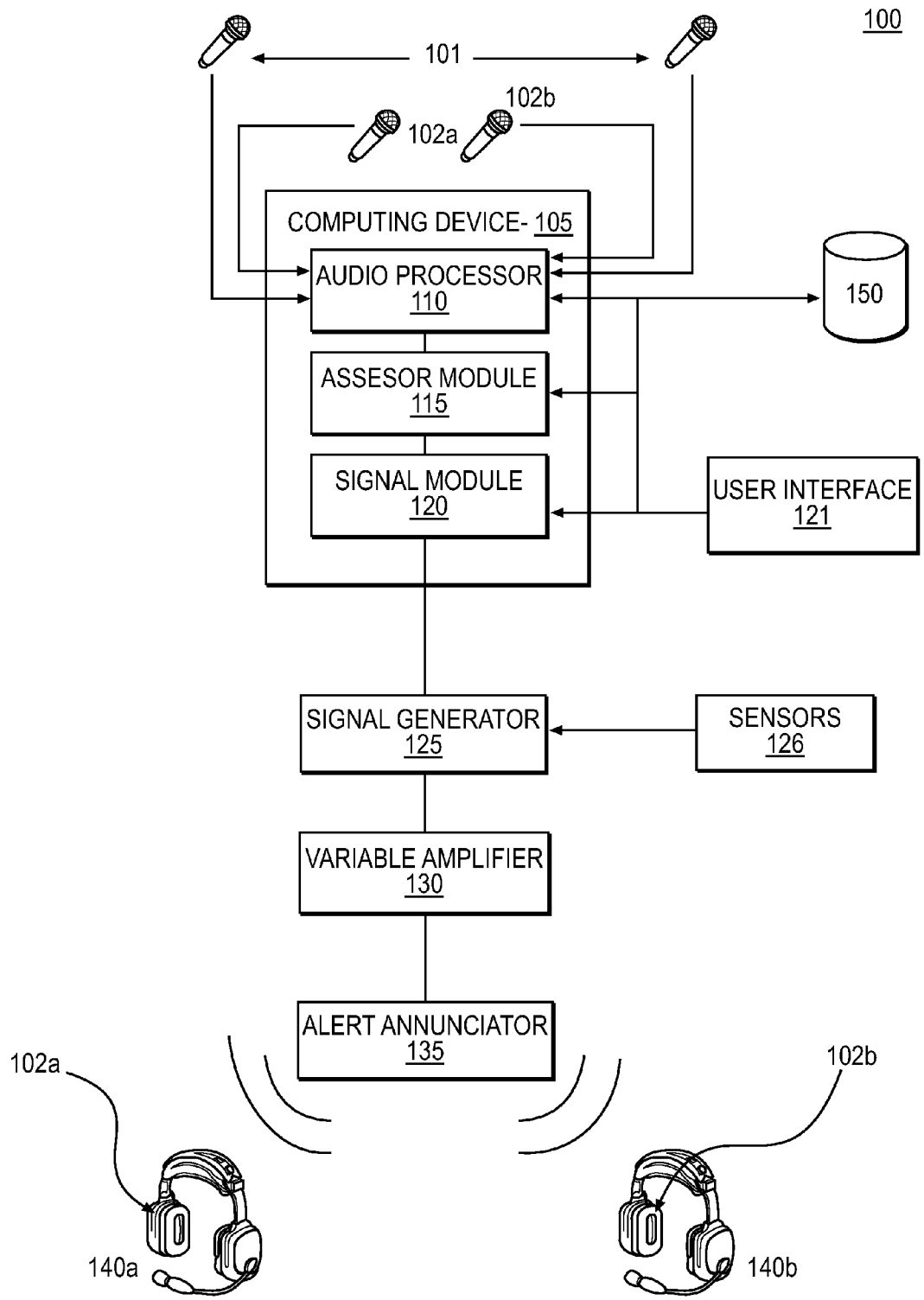
FIG. 1 is a functional block diagram of a system for enhancing aural signal detection.

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described herein generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, computing devices and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

In the following disclosure, the term "equipment space" is intended to read broadly and would encompass such exemplary equipment spaces as a cockpit, engine room of ships/boats, locomotives, electrical generating plants, factories and the like. Similarly the term "headset" is also to be read broadly to encompass such exemplary devices as communication headsets, Active noise reduction (ANR) headsets, passive external hearing protection devices (i.e., ear muffs), hearing aids and insertable earplugs of both the active and passive varieties. The term "sonic properties" as used herein is intended to be read broadly and would encompass sound qualities including, but not limited to, intensity, frequency, and timing of sound associated with one or more various discrete frequencies/frequency bands comprising a sound spectrum. The term "at-ear" means underneath a device's acoustic seal closest to an operator's eardrum, such as inside the ear cup of a headset or that part of an active or passive ear plug most proximal to the eardrum.

FIG. 1 is a simplified functional block diagram of an exemplary system 100 that may be used to support the various methods for auditory signal enhancement and detection. The system includes a computing device 105 that is configured with several modules to implement the methods disclosed herein below. The computing device 105 may be any appropriately configured computing device known in the art or that may be devised in the future. As non-limiting examples, the computing device may be a computer, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The computing device may be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The computing device 105 is a non-limiting example of a computer readable storage device.

The computing device 105 may include an audio processor 110. The audio processor 110 is in operable communication with the computer readable storage device 150 and microphones 101 and 102. As a general example, FIG. 1 illustrates two external microphones 101 and two at-ear microphones 102. However, the ideal number of external microphones 101 may range from a single microphone to three or more microphones, while the number of at-ear microphones 102 may range from zero to one or more microphones depending on the model and capabilities of the headsets or hearing protection devices 140(a-b) being utilized by the equipment operator(s). In equivalent embodiments, the headsets (140-a-b) may be passive or active earplugs. The external microphones 101 capture spectral and amplitude level characteristics of the ambient noise and are situated outside the headset acoustic seal. The microphone(s) 102 are situated under the headset acoustic seal and capture at-ear spectral and amplitude level characteristics.

The audio processor 110 receives an analog audio or sonic input from any number of external microphones 101 and at-ear microphones 102 within a space subjected to an ambient noise. The audio processor 110 may be any suitable analog-to-digital converter (ADC) as may be known in the art or that may be devised in the future that is configured to receive and convert analog sound signals to a digital format suitable for further analysis. The audio processor may retrieve and store data from the data store 150.

The audio processor 110 processes the real time ambient noise captured by the external microphones. The term "ambient noise" used herein is defined as the ambient noise as measured at a location in close proximity to an equipment operator. Therefore, when there are multiple equipment operators located in the same space, an external microphone 101 is preferably located in close proximity to each equipment operator to measure the ambient noise near the operator. In other equivalent embodiments where the equipment space is small (e.g., six feet across), a single external microphone 101 may suffice for multiple user headsets 140(a-b).

For example, when equipment operators wearing active (ANR) or passive headsets (140a-b), the external microphone 101 may be located integral with the headrest of the operator's seatback or on the headset. In other words, ambient noise measured by the external microphones 101 is not attenuated by the device's passive constructs in regard to passive headsets or by the passive constructs and active noise manipulation circuitry in regard to ANR headsets or hearing protection (140a-b).

In regard to the at-ear microphones 102(a-b), active headsets or active hearing protection devices typically have at-ear microphones 102(a-b) integrated inside the ear pieces of the headset, and located underneath the acoustic seal created by the headset or device. In the case of passive headsets or hearing protection devices, the headset may be modified to include an at-ear microphone 102. In embodiments where the headset is not modified to include an at-ear microphone 102, laboratory-measured sound attenuation information from the manufacturer or other entity, or label information from the Environmental Protection Agency (EPA) may be stored in a computer readable storage device (i.e., memory store) 150 and recalled by the system 100 to estimate the at-ear sound spectrum based on the measured ambient noise and the stored attenuation information. In some embodiments an equipment operator may manipulate a user interface 121 to select his headset from a menu of headsets that have attenuation data already stored in the data store 150. In other embodiments the equipment operator may enter the attenuation data manually via the user interface 121. The user interface 121 may be any one, or combination of various interface devices. Non-limiting examples of user interfaces 121 may include a cursor control device such as a joystick, a trackball, touch screen or touchpad, or a mouse and/or a keyboard.

The data store 150 may be a single data store or may be a plurality of cooperating data storage devices accessible by the computing device 105 or any component thereof. The data store 150 may store data describing spectral alteration characteristics (e.g., attenuation characteristics) of various types of passive and ANR headsets. The data store 150 may also store historical spectral and amplitude level characteristics of the ambient noise captured by the microphone(s) 101 and 102 as well as storing information regarding the identification and variable values needed to operate various alarm annunciators (e.g., loudspeakers) 135 that may exist in the equipment space subjected to an ambient noise level. The alarm anunciators may be loudspeakers external to the headsets/hearing protection (140a-b). In other embodiments the alarm annunciators 135 may be located beneath the acoustic seal of the headset (s)(140a-b)

After processing the ambient noise and/or at-ear sound into digital format by the audio processor 110, an Assessor Module 115 analyzes the spectra of the ambient noise and/or any at-ear sound. As will be discussed more fully below in regard to the method illustrated in FIG. 2, the Assessor Module 115 breaks down the spectra of the ambient noise and at-ear sound from each microphone 101 and/or 102 into full or ⅓-octave discrete frequencies from 125 to 8000 Hz and determines the intensity level at each specific frequency or frequency band. The Assessor Module 115 then passes the ambient or at-ear spectrum data to a Signal Module 120. Those of ordinary skill in the art will appreciate that ambient noise processing does not need to take place in real time. An alternative method, where the ambient noise and headset section are predictable and constant, may include measuring and recording the ambient noise once, evaluating the headset once and then use the recorded data to adjust the alerts at a future time.

The Signal Module 120 receives the ambient and/or at-ear spectrum data from the Assessor Module 115 and determines at what frequencies the intensity of the at-ear sound is at a minimum relative to the adjacent frequencies in the spectrum. Depending on the nature of the equipment space (e.g., a cockpit or a steam engine room), there may be a single relative minima in the at-ear spectrum or there may be multiple relative minima. One of ordinary skill in the art will appreciate that the relative minima may vary from environment to environment and application to application. The specific circuitry and/or programming of the Signal Module 120 utilized to capture the relative minima for a particular equipment space is therefore preferably dependent on the specific application. The Signal Module 120 may be hardware, software, firmware or any combination thereof.

Once the frequencies of the at-ear spectrum with the relative minima are identified, the Signal Module 120 artificially boosts the intensity of frequencies corresponding to the relative minima by applying a Masked Threshold ("MT" or "$L_{Tn}$") to the intensity of each frequency associated with a relative minimum. An exemplary MT of a specific ⅓-octave band or full octave band may be given by:

$$L_{Tn\ 1/3\ oct} = \max(L_{Nn\ 1/3\ oct}; L_{Tn-1\ 1/3\ oct} - 2.5\ \text{dB}) \quad \text{(Equation 1)}$$

An exemplary MT of a specific octave band may be given by:

$$L_{Tn\ oct} = \max(L_{Nn\ oct}; L_{Tn-1\ oct} - 7.5\ \text{dB}) \quad \text{(Equation 2)}$$

In other words the MT is equal to the greater of the actual intensity at the particular frequency in question or it is equal to the intensity of the next lower frequency of the spectrum minus 2.5 decibels for ⅓-octave band frequencies or minus 7.5 decibels for octave band frequencies. Those of ordinary skill in the art will appreciate that the MT may be established using other suitable formulae or similar methods without departing from the scope of this disclosure.

Once the at-ear frequency spectrum has been processed and the MT determined by the Signal Module 120, the resulting frequency spectrum is communicated to a signal generator 125. Signal generator 125 then creates a multi-frequency annunciation signal based on the masked threshold intensities of the relative minima frequencies of the at-ear spectrum such that the intensity of each of the frequencies comprising the signal is increased by +10-15 dB. The signal generator 125 may be any suitable signal generator known in the art or that may be devised in the future without departing from the scope of the subject matter disclosed herein.

The resulting signal from the signal generator 125 is then processed though a variable amplifier 130 to produce the intensities of the frequencies determined in the previous step and which comprise the multi-frequency annunciation signal. The signal is then broadcast into the equipment space by an alert anuciator 135.

The alert annunciator 135 may be any sound generating device that is configured to transmit multiple frequencies simultaneously or nearly simultaneously. A non-limiting example of an alert anunciator 135 may be an external loudspeaker or a loudspeaker at the ear of the user and underneath the acoustic seal. As a matter of hearing conservation, the sound intensity of any frequency generated by the alert annunciator 135 may be limited. As a non-limiting example, the maximum overall intensity level for any frequency may be limited to 85 dBA.

Figure 2:
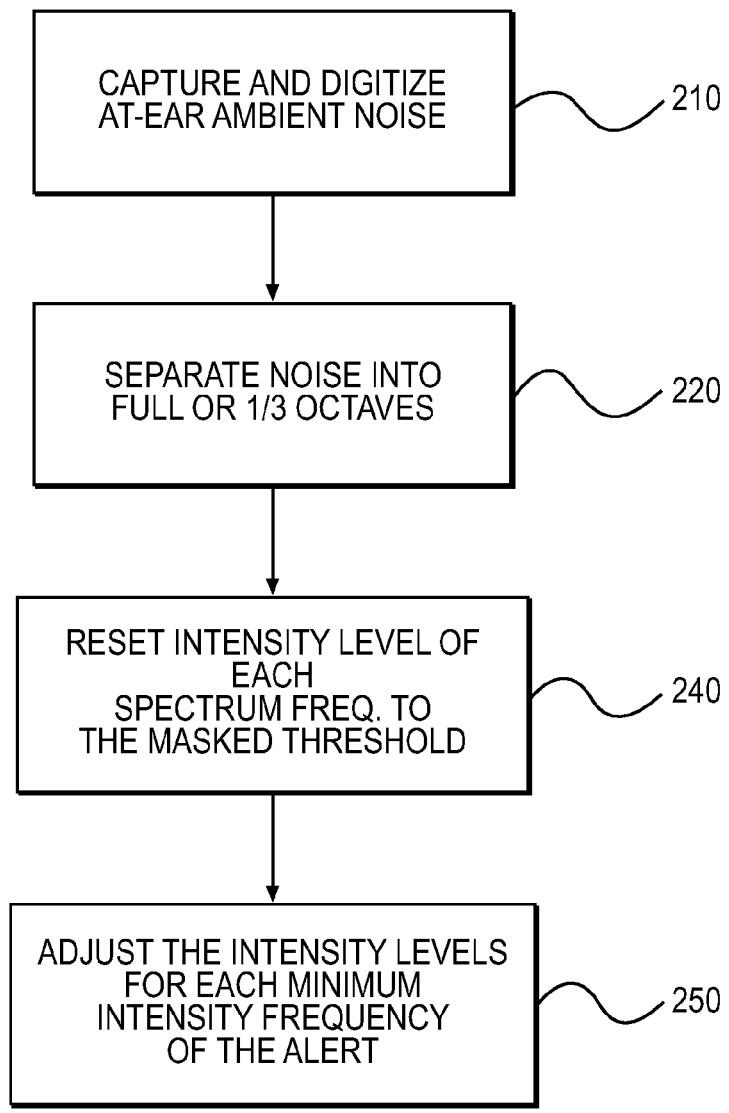
FIG. 2 is a flow diagram for a method to enhance aural signal detection with an active headset.

FIG. 2 is an exemplary method 200 for determining the desired at-ear ambient noise spectral qualities (i.e., intensity, frequency and timing) for a headset. Those of ordinary skill in the art will appreciate that the following method 200 for determining the at-ear ambient noise level and spectra is an exemplary method. The various processes of method 200 may be altered, combined, abbreviated or separated into sub-processes as may suit the needs of a system designer without departing from the scope of this disclosure.

At process 210, the intensity and spectral qualities of the operator's at-ear ambient noise is captured by the at-ear microphone 102 and digitized by the Audio Processor 110.

Thus, the ambient noise is captured from under the acoustic seal of the headset and reflects not only the inherent acoustical attenuation capability of the headset but also the quality of the fit to the equipment operator.

At process 220, Assessor Module 115 separates the ambient noise spectral level data into octave and/or ⅓-octave bands. An exemplary at-ear spectrum may break down as presented in Table 1 below.

TABLE 1

| | Frequency (Hz): | | | | | | | | | |
|---|---|---|---|---|---|---|---|---|---|---|
| | 125 | 250 | 500 | 630 | 1000 | 2000 | 3150 | 4000 | 6300 | 8000 |
| Ambient (dBA): | 92 | 84 | 80 | 80 | 79 | 74 | 70 | 68 | 66 | 66 |
| ANR Attenuation | 26.3 | 27.8 | 32.1 | 34.0 | 38.2 | 48.8 | 53.7 | 56.5 | 4.2 | 54.6 |
| At-ear noise (dBA): | 65.7 | 56.2 | 47.9 | 46 | 40.8 | 25.2 | 16.3 | 11.8 | 11.8 | 11.4 |
| ANR device (masked) | 65.7 | 63.2 | 60.7 | 58.2 | 55.7 | 53.2 | 50.7 | 48.2 | 45.7 | 43.2 |
| ANR device (+13 dBA) | 78.7 | 76.2 | 73.7 | 71.2 | 68.7 | 66.2 | 63.7 | 61.2 | 58.7 | 56.2 |

Note:
Bold values above indicate a Masked Threshold level higher than the actual intensity level At process 240, the spectrum intensities produced by the Assessor Module 115 at process 220 are examined by the Signal Module 120 to identify frequencies/frequency bands that have a relative intensity minimum in the spectra. For each octave or ⅓-octave band center frequency that is identified as having a relative minima, the signal module 120 resets the intensity level to the Masked Threshold (MT) (See e.g., See Table 1) plus a uniform intensity increase (e.g., 13 dBA). The Masked Threshold is defined according to Equation 1 or Equation 2 discussed above.

At process 250, signal generator 125 adjusts the intensities for each frequency/frequency band of the alert sound to the MT adjusted thresholds determined by the Signal Module 120 such that when an alarm condition is detected by sensors 126, the variable amplifier 130 may produce an alarm sound (s) that varies in frequency, intensity and timing from the ambient noise. Thus, the ability of the equipment operator to differentiate the alert signal from the ambient noise and detect it is enhanced. It should be noted that because the at-ear noise spectrum is determined directly by assessor module 115, the unique attenuation properties of the equipment operator's headset are inherently included in the masked intensities. These attenuation properties would not only include the rated attenuation of the headset structure itself but also includes any lessening of attenuation due to the fit of the headset to the operator or the lack thereof.

Figure 3:
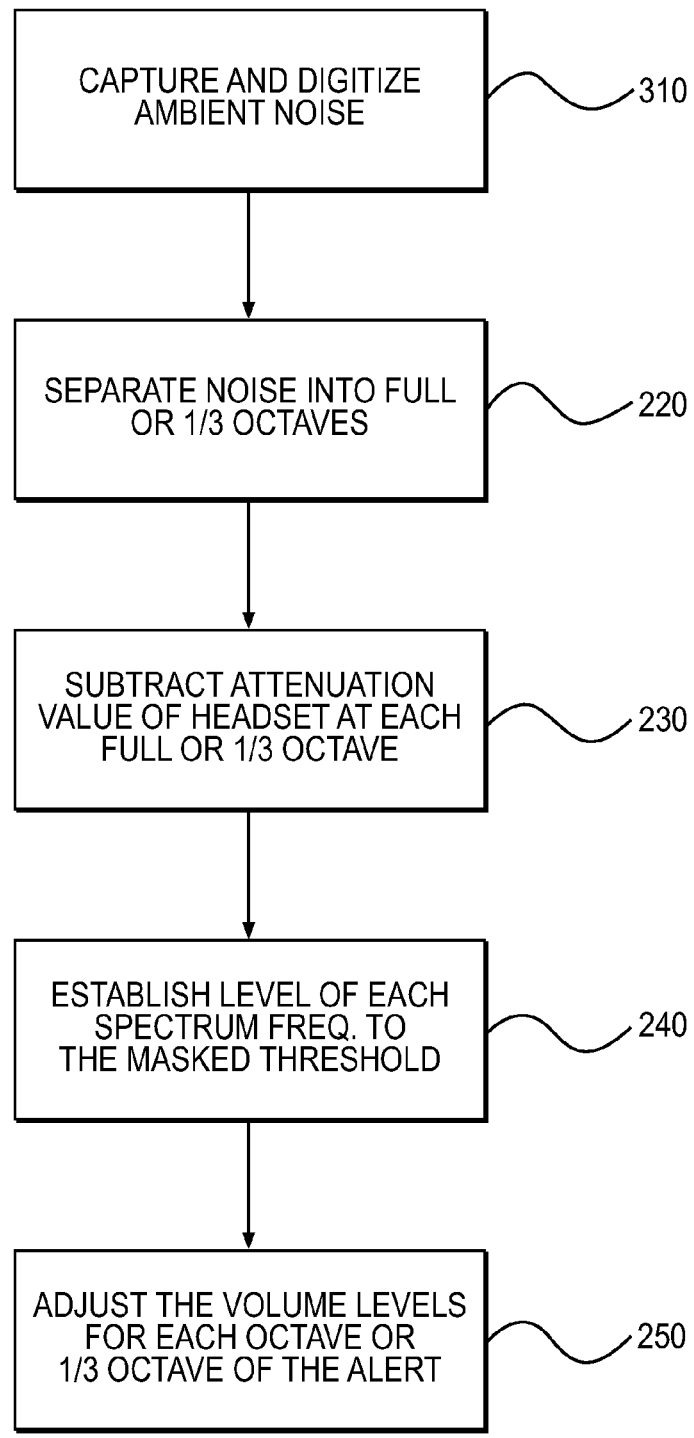
FIG. 3 is a flow diagram for a method to enhance aural signal detection with a passive headset.

FIG. 3 is another exemplary method 300 for determining the desired at-ear noise spectral qualities (i.e., level and frequency spectra) for a passive headset with no at-ear measurement microphone 102. Those of ordinary skill in the art will appreciate that the following exemplary method 300 for determining the at-ear noise level and spectra is a single exemplary method. The various processes of method 300 may be altered, combined, abbreviated or separated into sub-processes as may suit the needs of a system designer.

At process 310, the spectral qualities of the ambient noise in the vicinity of the equipment operator is captured by the external microphone 101 and digitized by the Audio Processor 110. Thus, the ambient noise is captured outside the acoustic seal of the headset. In preferred embodiments, the external microphone 101 may be integral to the operator's headrest. In other equivalent embodiments where the operator is mobile, the external microphone 101 may be a wireless microphone embedded in the headset or located on the operator's person.

At process 320, Assessor Module 115 separates the ambient noise spectral level data into octave or ⅓-octave intervals. An exemplary ambient spectrum may break down as presented in Table 2, below.

At process 330, the computing device 105 retrieves the rated spectral alteration characteristics (i.e., Attenuation Data) of the operator's headset 140 for each frequency/frequency band from the data store 150. The rated attenuation for each frequency/frequency band is then deducted from the ambient spectrum to produce an estimated at-ear noise level for each frequency as presented in Table 2, below.

At process 340, the estimated spectrum intensities produced at process 330 are examined by the signal module 120 for frequencies/frequency bands that have relative intensity minima in the spectrum. For each octave or ⅓-octave that is identified as having a relative minima, the Signal Module 120 sets the volume level to the Masked Threshold (MT) (See Table 3) plus a uniform intensity increase (e.g., 13 dBA). The Masked Threshold is defined according to Equation 1 discussed above.

TABLE 2

| | Frequency (Hz): | | | | | | | | | |
|---|---|---|---|---|---|---|---|---|---|---|
| | 125 | 250 | 500 | 630 | 1000 | 2000 | 3150 | 4000 | 6300 | 8000 |
| Ambient Spectrum(dBA) | 92 | 84 | 80 | 80 | 79 | 74 | 70 | 68 | 66 | 66 |
| Attenuation data (dBA) | 13.5 | 17.4 | 19.8 | 22.2 | 23.4 | 28.4 | 29.9 | 38.7 | 34.4 | 37.3 |
| Est. At-ear noise (dBA): | 78.5 | 66.6 | 60.2 | 57.8 | 55.6 | 45.6 | 40.1 | 37.3 | 31.6 | 27.8 |
| Passive device (MT) | 78.5 | 76.0 | 73.5 | 71.0 | 68.5 | 66.0 | 63.5 | 61.0 | 58.5 | 56.0 |
| Passive device (+13 dBA) | 91.5 | 89.0 | 86.5 | 84.0 | 81.5 | 79.0 | 76.5 | 74.0 | 71.5 | 69.0 |

Note:
Bold values above indicate a Masked Threshold level higher than the corresponding actual band level At process 350, signal generator 125 adjusts the intensities for each frequency/frequency band of the alarm sound to the MT adjusted thresholds (MT+13) determined by the signal module 120 such that when an alarm condition is detected by sensors 126, the variable amplifier 130 may produce an alert signal(s) that varies in frequency, intensity and/or timing from that of the ambient noise. Thus, the ability of the equipment operator to differentiate the alert signal from the ambient at-ear noise and detect it is enhanced. It should be noted that because the actual ambient spectrum is determined by assessor module 115, the singular attenuation properties of the equipment operator's headset are inherently included in the masked intensities by way of the rated or determined spectral alteration characteristics stored in data store 150. These attenuation properties would only include the rated or determined attenuation of the headset structure itself but and would not include any lessening of attenuation due to a poor fit or a poor acoustic seal of the headset.

Hence, given the final intensity levels of Table 2 (Passive Device (MT+13 dBA), the proper intensity for the 1000 Hz frequency that should be generated from an external loudspeaker is equal 104.9 dBA, which is the sum of the MT intensity of 81.5 dBA plus the attenuation of the headset of 23.4 dBA. Selected relative minimum frequencies determined in the spectrum would be generated with the intensities presented in Table 3.

TABLE 3

| | Frequency (Hz): | | | | | | | | | |
|---|---|---|---|---|---|---|---|---|---|---|
| | 125 | 250 | 500 | 630 | 1000 | 2000 | 3150 | 4000 | 6300 | 8000 |
| Ambient (dBA): | 92 | 84 | 80 | 80 | 79 | 74 | 70 | 68 | 66 | 66 |
| Passive device (+13 dBA) | 91.5 | 89.0 | 86.5 | 84.0 | 81.5 | 79.0 | 76.5 | 74.0 | 71.5 | 69.0 |
| Attenuation data (dBA) | 13.5 | 17.4 | 19.8 | 22.2 | 23.4 | 28.4 | 29.7 | 30.7 | 34.4 | 37.3 |
| Speaker Intensity (dBA) | 105.0 | 106.4 | 106.3 | 106.2 | 104.9 | 107.4 | 106.4 | 104.7 | 105.9 | 106.3 |

Similarly, for the active headset with the final at-ear ambient noise intensity levels of Table 1, selected relative minimum frequencies of the spectrum would be generated via the at-ear loudspeaker built into the ANR headset with the MT intensities presented in Table 1. Should it be necessary to annunciate an alarm from a loudspeaker external to the ANR headset, the spectrum intensity annunciated from the external speaker would include selected relative minimum frequencies from the spectrum in Table 4.

TABLE 4

| | Frequency (Hz): | | | | | | | | | |
|---|---|---|---|---|---|---|---|---|---|---|
| | 125 | 250 | 500 | 630 | 1000 | 2000 | 3150 | 4000 | 6300 | 8000 |
| Ambient (dBA): | 92 | 84 | 80 | 80 | 79 | 74 | 70 | 68 | 66 | 66 |
| ANR device (+13 dBA) | 78.7 | 76.2 | 73.7 | 71.2 | 68.7 | 66.2 | 63.7 | 61.2 | 58.7 | 56.2 |
| Attenuation data (dBA) | 26.3 | 27.8 | 32.1 | 34.0 | 38.2 | 48.8 | 53.7 | 56.5 | 54.2 | 54.6 |
| Speaker Intensity (dBA) | 105.0 | 104.0 | 105.8 | 105.2 | 106.9 | 115.0 | 117.4 | 117.7 | 112.9 | 110.8 |

In those situations where a single external annunciator 135 is required to annunciate an alert to more than one operator with a headset, the signal generator 125 may determine a single set of frequency intensities that is most likely to be detected by all operators wearing different headsets. The following methods for arriving at a single alarm spectrum that would provide an effective alert for all headsets in the equipment space are simplified and merely exemplary.

A first method of combining spectrums may include selecting the highest intensity for a given frequency/frequency band from among all of the determined speaker intensities. Thus, for the two exemplary spectrums provided in Tables 3 and 4 the single spectrum may be created by choosing the higher intensity of the of the two spectra as follows in Table 5.

TABLE 5

| | Frequency (Hz): | | | | | | | | | |
|---|---|---|---|---|---|---|---|---|---|---|
| | 125 | 250 | 500 | 630 | 1000 | 2000 | 3150 | 4000 | 6300 | 8000 |
| Speaker Intensity (ANR) | 105.0 | 104.0 | 105.8 | 105.2 | 106.9 | 115.0 | 117.4 | 117.7 | 112.9 | 110.8 |
| Speaker Intensity (Passive) | 105.0 | 106.4 | 106.3 | 106.2 | 104.9 | 107.4 | 106.4 | 104.7 | 105.9 | 106.3 |
| (Max: A or B) | 105.0 | 106.4 | 106.3 | 106.2 | 106.9 | 115.0 | 117.4 | 117.7 | 112.9 | 110.8 |

Another method may include determining the relative frequency intensity minima in each spectrum. Where there is a relative minimum intensity at a first frequency/frequency band in a first spectrum and a relative minimum intensity at a second frequency/frequency band in a second spectrum that is adjacent to or near the frequency with minimum intensity in the first spectrum, the speaker intensities for the two frequencies may interpolated into a single frequency for masking purposes using the magnitudes of the respective relative minima as a weighting factor between the two frequencies.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for producing an auditory alert that comprises sonic properties for an equipment operator wearing a headset prior to a presentation of the auditory alert to the equipment operator, the method comprising:
   measuring an at-ear ambient noise spectrum;
   separating the at-ear ambient noise spectrum into discrete, pre-determined frequencies;
   determining frequencies within the at-ear ambient noise spectrum that have relative minimum intensities;
   resetting the relative minimum sound intensity at each discrete, predetermined frequency exhibiting relative minimum intensity to a level that is equal to the higher of an actual intensity of each discrete, pre-determined frequency and an intensity of a next lower discrete, pre-determined frequency in the at-ear ambient noise spectrum minus 2.5 dBA for ⅓ octave bands and 7.5 dBA for full octave bands; and
   generating the auditory alert incorporating the enhanced relative minimum intensities.

2. The method of claim 1, wherein the headset is an active noise reduction headset.

3. The method of claim 1, wherein enhancing the magnitude of the relative minimum intensities further includes increasing the sound intensity of each pre-determined frequency by an incremental amount ranging from 10 dBA to 15 dBA.

4. The method of claim 2, wherein the auditory alert with enhanced relative minimum intensities is generated at an ear of the equipment operator.

5. A method for producing an auditory alert that comprises sonic properties to an equipment operator wearing a passive headset prior to the presentation of the auditory alert to the equipment operator, the method comprising:
   measuring an ambient noise spectrum in proximity to the equipment operator and outside an acoustic seal of the passive headset;
   determining and separating the ambient noise spectrum into discrete, pre-determined frequencies of an at-ear sound spectrum having relative minimum intensities from frequencies comprising the ambient noise spectrum;
   retrieving previously stored spectral alteration characteristics of the headset;
   enhancing a magnitude of the determined relative minimum intensities of the frequencies comprising the at-ear sound spectrum; and
   generating the auditory alert including the enhanced relative minimum frequency intensities.

6. The method of claim 5, wherein the previously stored spectral alteration characteristics of the headset includes sound attenuation magnitudes for each of the discrete, pre-determined frequencies.

7. The method of claim 5, wherein the previously stored spectral alteration characteristics of the headset are experimentally determined by one of a testing facility or from published data.

8. The method of claim 6, wherein determining frequencies within the at-ear sound spectrum includes subtracting the sound attenuation magnitudes for each of the discrete, pre-determined frequencies from the intensities at corresponding frequencies in the ambient noise spectrum.

9. The method of claim 5, wherein enhancing the magnitude of the relative minimum intensities of the at-ear sound spectrum includes resetting a sound intensity at each discrete, pre-determined frequency exhibiting relative minimum intensity to a level that is equal to the higher of an actual intensity of each discrete, pre-determined and an intensity of a next lower discrete pre-determined frequency in the at-ear sound spectrum minus 2.5 dBA for 13/octave bands and 7.5 dBA for full octave bands.

10. The method of claim 9, wherein enhancing the magnitude of the relative minimum intensities further includes increasing the sound intensity of each pre-determined frequency by an incremental amount ranging from 10 dBA to 15 dBA.

11. The method of claim 10, wherein the auditory alert with the enhanced minimum intensities is generated by an external speaker.

12. A system configured to produce an auditory alert comprising sonic properties to an equipment operator wearing a headset prior to a presentation of the auditory alert to the equipment operator, the system comprising:
   a microphone;
   a computing device in operable communication with the microphone, wherein the computing device is configured to process at-ear sound data received from the microphone into an alert signal by separating the ambient noise spectrum into discrete, pre-determined frequencies enhancing magnitudes of the relative minimum intensities of the at-ear sound spectrum including and resetting a sound intensity at each discrete, pre-determined frequency exhibiting relative minimum intensity to a level that is equal to the higher of an actual intensity of each discrete, pre-determined and an intensity of a next lower discrete pre-determined frequency in the at-ear sound spectrum minus 2.5 dBA for 13/octave bands and 7.5 dBA for full octave bands;
   a signal generator configured to create the alert signal; and
   an alert annunciator configured to annunciate the alert signal.

13. The system of claim 12, wherein the computing device includes an assessor module configured to spectrally analyze the at-ear sound data.

14. The system of claim 13, wherein the computing device includes a Signal Module in operable communication with the Assessor Module, the Signal Module being configured to determine at what frequencies the intensity of the at-ear sound data is at a minimum relative to adjacent frequencies in the at-ear sound data.

15. The system of claim 12, further comprising storing and retrieving attenuation characteristics of the headset from one or more memory devices.

* * * * *